US006622094B2

(12) United States Patent
Still et al.

(10) Patent No.: US 6,622,094 B2
(45) Date of Patent: *Sep. 16, 2003

(54) METHOD FOR DETERMINING RELATIVE ENERGIES OF TWO OR MORE DIFFERENT MOLECULES

(75) Inventors: W. Clark Still, New York, NY (US); Quentin McDonald, New York, NY (US)

(73) Assignee: The Trustees of Columbia University in the City of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/601,734

(22) Filed: Feb. 15, 1996

(65) Prior Publication Data

US 2003/0055574 A1 Mar. 20, 2003

(51) Int. Cl.[7] .............................................. G06F 17/50
(52) U.S. Cl. ............................................ 702/27; 703/12
(58) Field of Search .............................. 364/496, 497, 364/498, 499, 578; 702/19, 27, 32; 703/11, 12

(56) References Cited

U.S. PATENT DOCUMENTS

| | | | | |
|---|---|---|---|---|
| 4,855,931 A | * | 8/1989 | Saunders | 364/499 |
| 5,265,030 A | * | 11/1993 | Skolnick et al. | 364/496 |
| 5,434,796 A | * | 7/1995 | Weininger | 364/578 X |
| 5,600,570 A | * | 2/1997 | Imasato et al. | 364/496 |

FOREIGN PATENT DOCUMENTS

WO    WO 93/20075    * 10/1993

OTHER PUBLICATIONS

Allen, M.P. and Tildesley, D.J. "Monte Carlo Methods", Computer Simulation of Liquids, Claredon Press, Oxford, 1987, pp. 110 139.*

Chandler, D., "Monte Carlo Method in Statistical Mechanics" Introduction to Modern Statistical Mechanics, Oxford University Press, 1987, pp. 159–183.*

Kollman, P. "Free Energy Calculation: Application to Chemical and Biochemical Phenomena" Chem. Rev., 1993, 93: 2395–2417.*

Senderowitz et al., "A Smart Monte Carlo Technique for Free Energy Simulations of Multi conformational Molecules. Direct Calculations of the Conformational Populations of Organic Molecules" J. Amer. Chem. Soc., 1995, 117: 8211–8219.*

(List continued on next page.)

Primary Examiner—M Kemper
(74) Attorney, Agent, or Firm—John P. White; Cooper & Dunham LLP (57) ABSTRACT

The present invention provides for a method for selecting a molecule for a population which comprises: a) selecting a first molecule with a conformation characterized by a particular set of coordinates that define the position of each atom in the first molecule; b) determining the energy of the first molecule; c) transforming the coordinates of the first molecule to the coordinates of a second structurally distinct molecule to produce a particular conformation of the second molecule characterized by a particular set of coordinates that define the position of each atom in the second molecule; d) determining the energy of the second molecule; thus, selecting either the first molecule or the second molecule for the population based on their relative energies. The selected molecule may be redefined as the first molecule and the procedure repeated iteratively so as to obtain a population of first molecules and a population of second molecules. Based on the populations, the free energy difference between the first molecule and the second molecule may be determined.

22 Claims, 2 Drawing Sheets

OTHER PUBLICATIONS

Wimmer, E., "Computational Materials Design with First-Principles Quantum Mechanics" Science, 1995, 269:1397–1398.* van Gunsteren et al., "On the Interpretation of Biochemical Data by Molecular Dynamics Computer Simulation" Eur. J. Biochem 1992, 204(3): 947–961.* van Gunsteren et al., "Methods for Calculation of Free Energies and Binding Constants: Successes and Problems", Computer Simulation of Biomolecular Systems, Theoretical and Experimental Applications ESCOM, 1989, p. 27–59.*

Hellinga et al "Optimal Sequence Selection in Proteins of Known Structure by Simulated Evolution" Biochemistry v. 91 pp 5803–5807, Jun. 1994.*

Amisaki et al. "Molecular Dynamics and Free Energy Perturbation Calculations on the Mutation of Tyrosine 45 to Tryptophan in Ribonuclease $T_1$" Chem. Pharm. Bull. 40(5) p. 1303–1308, 1992.*

Heiner et al. "Structure Prediction on Subtilisin BPN' Mutants Using Molecular Dynamics Methods" Protein Engineering 6(4) p. 397–408, 1993.*

Rossi et al. "Application of the Free Energy Perturbation Method to Human Carbonic Anhydrase II Inhibitors" Journal of Medicinal Chemistry v. 38 n 12 p. 2061–2069, Jun. 1995.*

Guarnieri, F. and Still, W.C. *J. Comput. Chem.* 1994, 15, 1302–1310.

Liu, R. and Still, W.C. *Tetrahedron Lett.* 1993, 34, 2573.

Liu, R. *Philosophical Transactions of the Royal Society Series A*, 1993, 245, 97.

McDonald, D.Q. and Still, W.C., *Tetrahedron Lett.* 1992, 33, 7743.

Schneider, I., *Genetic and Engineering News*, Oct. 1, 1995, 8.

Still, W.C., Tempczyk, A., Hawley, R.C. and Hendrickson, T. *J. Am. Chem. Soc.* 1990, 112, 6127.

* cited by examiner

Given two molecules (A and B) with coordinates that define the positions of their atoms,
1. Randomly choose one molecule (e.g. A)
2. Define this molecule as the starting molecule
3. Initialize the populations ($N_A$ and $N_B$) of A and B as zero.

Compute starting molecule's energy ($E_{start}$)

1. Replace the other molecule's coordinates with the starting molecule's coordinates.
2. Define this other molecule with it's new coordinates as the trial molecule.
3. Optionally modify the trial molecule's coordinates systematically to make the modified coordinates correspond to a relatively low energy state of the trial molecule.
4. Optionally modify the trial molecule's coordinates by traditional Monte Carlo or molecular/stochastic dynamics methods.

Compute the trial molecule's energy ($E_{trial}$)

Select either to starting molecule or the trial molecule using the Metropolis Monte Carlo procedure based on $E_{start}$ and $E_{trial}$.

Add 1 to the population ($N_A$ or $N_B$) of the selected molecule (A or B)

Redefine the selected molecule as the starting molecule and save it's energy as $E_{start}$ Iterate until the population ratio $N_A/N_B$ stabilizes Done Compute free energy difference between molecules A and B from their populations:
$\Delta G_{A-B} = -RT \ln(N_A/N_B)$

METHOD FOR DETERMINING RELATIVE ENERGIES OF TWO OR MORE DIFFERENT MOLECULES

The invention disclosed herein was made with Government support under Grant No. CHE 92-08254 from the National Science Foundation. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

One of the most important applications of computational chemistry is the prediction of the properties of new chemical compounds. If such predictions could be reliably made, then new materials or compounds having desirable properties could be designed rationally. Unfortunately, reliable property prediction is very difficult to achieve. One of the most sought after property predictions is found in the pharmaceutical industry. There, chemists often hypothesize dozens of molecules they might synthesize but have trouble deciding which ones have the best chance of being highly active in some biological assay.

Researchers have tried for many years to calculate the relative binding energies of closely related drug molecules for biological and chemical receptors using free energy perturbation or thermodynamic integration (Kollman, 1993). Such methods gradually mutate one drug into another over many (10–100) stages and such multistage methods are not only slow, but they have not proven to be truly predictive. Because of recent advances in molecular biology and x-ray crystallography, the three-dimensional molecular structures of many biological target proteins are now known. In theory, the knowledge of the structure of the target protein could be used to rationally design hypothetical molecules that strongly bind the target protein. Such molecules would then be candidates for actual chemical synthesis. Unfortunately, the calculations are quite complex from a thermodynamic standpoint. The current approaches to predictions of drug-protein binding energies are too inaccurate and too slow to be used for practical drug design. The invention described herein provides a solution to this problem.

SUMMARY OF THE INVENTION

The present invention provides for a method for selecting a molecule for a population which comprises: a) selecting a first molecule with a conformation characterized by a particular set of coordinates that define the position of each atom in the first molecule; b) determining the energy of the first molecule; c) transforming the coordinates of the first molecule to the coordinates of a second structurally distinct molecule to produce a particular conformation of the second molecule characterized by a particular set of coordinates that define the position of each atom in the second molecule; d) determining the energy of the second molecule; thus, selecting either the first molecule or the second molecule for the population based on their relative energies. The selected molecule may be redefined as the first molecule and the procedure repeated iteratively so as to obtain a population of first molecules and a population of second molecules. Based on the populations, the free energy difference between the first molecule and the second molecule may be determined.

DETAILED DESCRIPTION OF THE INVENTION

The present invention provides for a method for selecting a molecule for a population which comprises: a) selecting a first molecule with a conformation characterized by a particular set of coordinates that define the position of each atom in the first molecule; b) determining the energy of the first molecule; c) transforming the coordinates of the first molecule to the coordinates of a second structurally distinct molecule to produce a particular conformation of the second molecule characterized by a particular set of coordinates that define the position of each atom in the second molecule; d) determining the energy of the second molecule; thus, selecting either the first molecule or the second molecule for the population based on their relative energies. The selected molecule may be redefined as the first molecule and the procedure repeated iteratively so as to obtain the free energy difference between the first molecule and the second molecule. The method may be repeated iteratively so as to generate a population of selected first molecules and a population of selected second molecules. The method may be repeated iteratively so as to generate a stable population of selected first molecules and a stable population of selected second molecules. The free energy difference between the first molecule and the second molecule may be determined from the stable population of selected first molecules and the stable population of selected second molecules. Either the first molecule or the second molecule may be chosen based on the free energy difference between the first molecule and the second molecule.

In one embodiment, the first molecule or the second molecule or both molecules may be subjected to extrinsic forces from an environment which is either a solvent or a vacuum. Either the first molecule or the second molecule or both molecules may be subjected to extrinsic forces from an environment which is defined by a continuum model for salvation or from an environment containing one or more molecules. The environment may include water, organic solvents, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

In one embodiment, the determination of the energy of the first molecule or the second molecule may be via molecular mechanics, semi-empirical methods or quantum mechanics. The selection of either the first molecule or the second molecule based on their relative energies may include selection via a Boltzmann calculation, a probability calculation, a Metropolis transition probability calculation or a Monte Carlo calculation.

The molecular coordinates of this embodiment may be external or internal coordinates. The external coordinates may be Cartesian coordinates. The internal coordinates may be bond lengths, bond angles or torsion angles. For systems having multiple molecules, additional internal coordinates specify the relative positions and orientations of each of the molecules so as to define the position of each atom in the system.

The coordinates of the first molecule may be transformed systematically, randomly, or both systematically and randomly to produce the conformation of the second molecule. The coordinates of the first molecule may be systematically modified so as to produce the conformation of the second molecule, which conformation is relatively low in energy. The coordinates of the first molecule may be transformed to produce the coordinates of the second molecule with randomization of one or more of the coordinates of the first molecule. The coordinates of the first molecule or the coordinates of the second molecule may be modified randomly or systematically. The coordinates of the first molecule or the coordinates of the second molecule may be modified by molecular, stochastic, Langevin or Brownian dynamics as part of the transformation. The coordinates may be modified by Monte Carlo methods or the like as part of the transformation.

In one embodiment, dummy atoms may be used to represent atoms that are absent in the first molecule but present in the second molecule, or alternatively present in the first molecule but absent in the second molecule.

The free energy difference between the first and second molecules varies with environment and the method may be applied in environments which may include vacuum, water, an organic solvent, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

In another embodiment of the present invention, the populations and free energy differences may be calculated by a computer which processes data representing the physical or energetic characteristics of first molecule and the second molecule and conformations thereof.

The method of the present invention may be used to select a drug candidate, to design catalysts to stabilize transition states, or to design new media for the separation and/or purification of molecules. The method of the present invention may be used to design molecules which bind a transition state analog or a transition state. The present invention may be used to compare crystal structures or calculate spectra or other physical properties of a molecule. The present invention may be used to design media to purify biomolecules or specific kinds of molecules, such as enantiomers.

As used herein, a molecule may be a single molecule or a molecular system. A molecular system may include one or more molecules.

As used herein, the term coordinates encompasses measurements that define atomic positions in a particular three dimensional state of a molecule or molecular system. A complete set of coordinates defines the position of all atoms in a molecule or molecular system. Coordinates may be external or internal. External coordinates are measured relative to an external framework (e.g. Cartesian (x, y, x) coordinates for the atoms in a molecule). Internal coordinates are measured relative to other atoms in the molecule (e.g. bond lengths, bond angles and torsion angles). For systems having multiple molecules, additional internal coordinates are needed to specify the relative position and relative orientation of each molecule so as to define the position of every atom.

As used herein, the term conformation encompasses any particular three dimensional state of a molecule. Molecules usually exist in many different three dimensional states and each such distinct state is described as a conformation.

As used herein, the term population encompasses the fraction of molecules in a given sample that exist in a given conformation or set of conformations. Populations are usually expressed as a number between 0.0 and 1.0, and are symbolized as N (i.e. N=0.0–1.0). A conformation has a population of 0.0 if none of the molecules are in that conformation. A conformation has a population of 0.5 if half of the molecules are in that conformation and the other half of the molecules are in other conformations. A conformation has a population of 1.0 if all of the molecules are in that conformation.

As used herein, the term free energy encompasses Gibbs (usually symbolized as G) or Helmholtz (usually symbolized as A) free energy associated with molecular thermodynamics. Free energy is a thermodynamic function designed to provide a criterion for spontaneous changes. It is defined in terms of enthalpy and entropy through the equation G=H−TS, where S is entropy, T is temperature and H is enthalpy. The free energy difference between any two states (e.g. states 1 and 2) is related to the populations of those states ($N_1$ and $N_2$ respectively) by a classical equation from molecular thermodynamics:

$$\text{Free energy difference} = -RT \ln(N_1/N_2)$$

where R is the thermodynamic gas constant (~1.987 cal/deg mol), T is the temperature in degrees Kelvin and ln symbolizes a natural logarithm.

As used herein, the term ensemble encompasses a collection of a large number of states of a system that is constructed so as to approximate the macroscopic thermodynamic properties of that system at a given temperature. In the ensembles described herein, all the states of the system (e.g. the conformations) in an ensemble are assumed to be in thermodynamic equilibrium with one another and have populations in accord with such an equilibrium. Ensembles useful with the method described herein are the canonical ensemble and the microcanonical ensemble as described in Allen and Tildsley, 1987.

As used herein, the term extrinsic forces encompasses the forces that originate from the environment of a molecule or molecular system and act on the atoms of that molecule or molecular system. These forces originate from other molecules or models representing other molecules in the vicinity of the first molecule or the second molecule. The other molecules may be solvent molecules, other solute molecules, or both. Models useful for representing the other molecules include continuum solvent models, pseudoreceptor models, united atom models or other models based on reduced particle representations of molecules or atoms.

Another embodiment of the present invention is a method for predicting a relative binding free energy between a first molecule and a second molecule each for a third molecule which includes using the method described herein with the first molecule free and the second molecule free and the first molecule and the second molecule interacting with the third molecule.

The embodiment described in the present invention may be performed by a computer which computer processes data which represents the physical or energetic characteristics of the first molecule free and the second molecule and the first molecule and the second molecule interacting with the third molecule.

Another embodiment of the present invention may be an apparatus for selecting a molecule for a population which includes: a) a means of selecting a first molecule with a conformation characterized by a particular set of coordinates that define the position of each atom in the first molecule; b) a means of determining the energy of the first molecule; c) a means of transforming the coordinates of the first molecule to the coordinates of a second structurally distinct molecule to produce a particular conformation of the second molecule characterized by a particular set of coordinates that define the position of each atom in the second molecule; d) a means of determining the energy of the second molecule; thus, selecting either the first molecule or the second molecule for the population based on their relative energies. The selected molecule may be redefined as the first molecule and the procedure repeated iteratively so as to obtain the free energy difference between the first molecule and the second molecule. The method may be repeated iteratively so as to generate a population of selected first molecules and a population of selected second molecules. The method may be repeated iteratively so as to generate a stable population of selected first molecules and a stable population of selected second molecules. The free energy difference between the first molecule and the second molecule may be determined from the stable population of selected first molecules and the stable population of selected second molecules. The first molecule or the second molecule may be chosen based on the free energy difference between the first molecule and the second molecule.

The present invention provides for the use of a workstation computer, a supercomputer or a personal computer. In particular, hardware suitable for carrying out the present invention could also include any fast digital processor, specifically, UNIX workstations (i.e. Silicon Graphics IRIS, INDIGO, INDIGO$^2$, IBM RS/6000; Hewlett Packard Model 9000) and supercomputers (e.g. CRAY Y-MP, IBM SP1 and SP2). For graphical display of results, IBM RS/6000 and Silicon Graphics IRIS, INDIGO or INDIGO$^2$ graphics workstations may be used.

For calculations of the relative binding energies of different drugs to a given protein receptor to provide reliable information, many different factors have to be taken into account. In particular, the gas phase potential energy force field has to be accurate, the effect of solvent has to be included in some realistic and efficient way, and representative vibrational and conformational states of the system have to be sampled with the appropriate Boltzmann weights. This last issue is known as the sampling problem and it is a particularly difficult one to solve because the drug-receptor complex may exist in many different conformations. Furthermore, these different conformations may be separated by large energy barriers that prevent these conformations from being interconverted using traditional simulation methods. If a simulation cannot interconvert all significantly populated conformations rapidly, then the simulation will not be able to assess the relative contributions for the various conformations to the overall binding energies. Because barriers between conformations as high as 10 kcal/mol are common and are crossed on the time scale of microseconds ($10^{-6}$ seconds), it is clear that traditional simulation methods which assess time scales on the order of a nanosecond ($10^{-9}$ seconds) are incapable of modeling conformationally flexible biological systems accurately. Recent studies (van Gunsteren and Mark, 1992) suggest that the length of contemporary free energy simulations of flexible biological molecules may be orders of magnitude too short for convergence and any agreement with experiment may be only fortuitous (i.e. not predictive). In order to compute statistically reliable thermodynamic properties (e.g. binding free energies) for a conformationally flexible system, it is essential that all different conformations of the system be sampled many times in a simulation at the temperature of the experiment to be reproduced or predicted.

A number of new algorithms have been developed to speed such simulations significantly. These include continuum models for solvent (GB/SA model) and barrier-hopping molecular simulation methodology (MC/SD and JBW methods). Current approaches to calculating the relative binding energies of different molecules involve mutating one molecule into another over many (usually 10–100) intermediate stages. And because each stage has to be sampled over all possible states (the sampling problem has to be solved for each of these many states), the overall multistage simulation is extremely slow to generate a final accurate answer.

Two methods that have been applied to calculating the binding energy of different molecules are free energy perturbation (FEP) and thermodynamic integration (TI). These methods use MD (molecular dynamics) or MC (Monte Carlo) as an ensemble-generating method and then apply the classical equations below for computing the free energy (G) between two states A and B (e.g. two different drug molecules) given the structures in the ensemble:

$$\text{FEP Equation}: G_B - B_A = \sum -RT \ln < e^{-(V_{\lambda B} - V_{\lambda A})/RT} >\lambda A$$

$$\text{TI Equation}: G_B - B_A = \int < \partial V(\lambda)/\partial \lambda >_\lambda d\lambda$$

where R is the thermodynamic gas constant, T is the temperature in degrees Kelvin, V is the potential energy and $\lambda$ is a coupling parameter that varies from 0.0 (where the state is A) to 1.0 (where the state is B) (van Gunsteren and Weiner, 1989). In both cases, the summation and the integration are taken over a great many stages from $\lambda=0.0$ to $\lambda=1.0$ (e.g. $\lambda=0.0, 0.05, 0.10 \ldots 1.0$). The multistage aspect of these calculations makes them particularly slow (typically weeks of time on a fast computer). In addition, these simulations involve nonphysical intermediate states that make it difficult to analyze the structural origins of any free energies thus calculated.

The invention described herein, simulated mutational equilibration (SME) operates differently and allows the simulation to be carried out in a single stage (and thus to converge 2–100 times faster than standard free energy calculating methods). Thus, unlike FEP and TI in which all intermediate stages (all values of $\lambda$) must be completed before a final result can be obtained, SME gives continuous estimations of the final result that become more and more precise as the simulation continues. Furthermore, SME can be used in conjunction with GB/SA salvation and JBW simulation methodology to speed the overall calculation. Taken together, it appears that these methods will allow a very much improved solution to the key problem in quantitative drug design.

SME also differs from previous methods in that it does not use the FEP or the TI equations. Instead, it uses a modification of a basic equation giving the free energy (G) difference between two different states (A and B):

$$\text{SME Equation: } G_B - B_A = -RT \ln <N_B/N_A>_{AB}$$

where $N_A$ and $N_B$ are the populations of two different kinds of molecules (A and B respectively) that are in thermodynamic equilibrium (designated by $<>_{AB}$). The SME equation above is written for two different states (A and B) but it can be extended to more states in the classical way. While a thermodynamic equilibrium between different chemical compounds cannot usually be established in the real world because there is no general way to interconvert different kinds of molecules (i.e. to somehow mutate one molecule into a different molecule), such mutational equilibration can be carried out by a computer simulation of the process.

Thus, in one embodiment of this invention, SME computes molecular free energy differences via the SME equation above by simulating an equilibration between two different molecules to give their relative amounts (i.e. their populations) at a simulated thermodynamic equilibrium. To carry out such a simulation, a Monte Carlo (MC)—like procedure may be used (Allen and Tildesley, 1987). The traditional MC molecular simulation procedure involves making random changes in the coordinates of atoms in one or more molecules. SME, however, is distinguished from traditional MC in that it includes random interconversions between molecules of different chemical compounds. This MC-like random interconversion of molecules of different chemical compounds as well as changes (random or systematic) to the coordinates of their atoms is the central characteristic of our SME invention. With traditional MC, a test based on relative energy (e.g. the standard Metropolis test) is applied to each newly randomized molecular coordinate set and the new coordinate set is accepted and added to the generated ensemble only if the test is passed. In SME, the same energetic testing and acceptance procedure is applied to the randomly selected chemical molecules. In the limit of a long SME simulation in which the average properties of the ensemble have become stable (i.e. the simulation is converged), the relative populations of two (or more) different chemical compounds at equilibration can be determined by simply counting the number of times each different chemical compound appears in the generated ensemble. The SME equation above then gives the relative free energies of the two different molecules.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

An S M E Method

In one embodiment of this invention the basic SME procedure that generates a thermodynamic ensemble of different chemical compounds is as follows:

a) given a set of different chemical compounds (termed SET), each different chemical compound being characterized by molecules having a certain array of atoms and bonds;

b) select one of the chemical compounds from SET and an array of coordinates for each atom in a molecule of the selected chemical compound, which chemical structure is termed L;

c) randomly select another chemical compound from SET and assign to it coordinates that are derived from the coordinates of the atoms in molecule L, which new chemical structure molecule is termed M;

d) choose L or M based on their relative energies (e.g. using the Metropolis test);

e) add the chosen molecule to the ensemble and redefine that molecule as L;

f) go to step c).

In this procedure, steps c) through f) are repeated until the average properties of the generated ensemble of molecular structures become stable in time (i.e. that the simulation is converged). The total number of molecules in the system is constant over the course of the simulation. While the above procedure will give the correct ensemble in the limit of a very long simulation, the basic SME procedure can be carried out in various ways to make it more efficient. For example, in deriving the atomic coordinates of M from those of L, the atomic coordinates of L may be transferred to the atoms of M directly, or they may be transferred with additional variation in some random or non-random way. Random ways of coordinate variation include traditional MC variation. Non-random ways of coordinate variation could include variations based on molecular (MD) or stochastic (SD) dynamics. Non-random ways of coordinate variation could also include systematic variations that cause the L-atom coordinates to become coordinates that are relatively low in energy when assigned to structure M. Additionally, traditional ensemble-generating procedures (MC, MD or SD) can be applied to structure L or M at various points in the SME procedure to improve the algorithm's exploration of phase space and thus to improve efficiency.

There are a number of practical issues for implementing the SME procedure to compute the free energy difference between any pair of molecules in the general case. One issue is that two molecules may have absolute energies that are very different because their chemical structures are very different. Thus, if the energies differ by more than ~2 kcal/mol, the higher energy species will be found with only a very small population and this makes it difficult to obtain a reliable estimate of the population ratio $P_B/P_A$. In that case, a constant ($G_k$) can be subtracted from the energy of one of the structures to approximately equalize their energies during the SME simulation. After the simulation is complete, $G_K$ can then be added to the population-based free energy difference (SME equation) to give the actual free energy difference. Another issue emerges when molecules in SET are structurally very different (e.g. have different basic structures, different substituent patterns, different numbers of atoms or groups). In such cases, atoms may exist in molecule M that have no corresponding atom in molecule L. Such atoms are termed noncorresponding atoms. There are a number of ways to assign coordinates to noncorresponding atoms. One method is to use analytical geometry to construct their coordinates from the positions of atoms in L that do have correspondents in M. Another method is to add a dummy atom to L for each noncorresponding atom in M. Such dummy atoms have zero energetic parameters that prevent them from interacting with other (not dummy) atoms in L. Thus, the dummy atoms in L act as place holders for noncorresponding atoms in M while not effecting the properties of L.

One of the most valuable applications of the SME procedure is the calculation of relative binding energies of different molecules for some other third molecule. One application is the drug binding problem in which the relative binding energies of a set of different drug candidates and some biological receptor (e.g. a protein) are to be predicted. To carry out such a calculation, two SME calculations are carried out. In the first SME calculation, the free energy difference ($\Delta G_{unbound}$) between a pair of different molecules in the absence of a third molecule is carried out. This calculation would typically be carried out in an environment of some appropriate solvent. In the second SME calculation, the free energy difference ($\Delta G_{unbound}$) between the same pair of different molecules in the presence of the third molecule (e.g., a biological receptor) is carried out. This calculation would typically be carried out in the same solvent as the first calculation. The relative binding free energy of the two molecules for binding the third molecule is then given by the difference in the free energy results of the two SME calculations ($\Delta G_{bound} - \Delta G_{unbound}$).

Another advantage of the present invention is that the SME method involves direct interconversion of molecules of interest without the necessity of interconversions via nonphysical, intermediate states. This feature allows the structural basis of relative drug binding to be readily analyzed to determine the reason one drug molecule binds better than another and thus to learn how to design even better drug molecules. One embodiment of the subject invention is rational drug design.

Example 2

Enantioselectivity of Binding of Peptides to a Synthetic Host Molecule

The present invention may be used as a tool for drug candidate selection and for the design of catalysts to stabilize chemical reaction transition states. A specific application of the SME procedure is to compute the free energy difference of binding of two different molecules (here several enantiomeric peptides) for a third molecule (here several synthetic host molecules). In this example, the invention is used to determine the enantioselectivity of binding of peptides to a synthetic host molecule.

The peptide-binding host molecule 1 had recently been synthesized and its binding of peptides characterized (Liu and Still, 1993; Still and Liu, 1993). Receptor 1 was found to bind the alanine-derived peptides 2 and 3 strongly in chloroform solution and with a strong preference for the L-form of alanine. Peptide 4 was bound weakly and with only a small preference for the L-form. A conformational isomer of 1 (inv-1) was found to bind both the D- and L-forms of peptide 2 though weakly and with poor selectivity. Twenty-stage free energy perturbation (FEP) calculations were successful in approximately reproducing the observed selectivity. Below is described how single-stage simulated mutational equilibrium (SME) calculations can also reproduce experiment and do so more efficiently than can FEP calculations.

1a) R = CH$_2$Ph
1b) R = CH$_3$

2  R = Boc;  R' = NHMe
3  R = MeO$_2$C;  R' = OtBu
4  R = Boc;  R' = OMe

Methods

All simulations were performed using the united atom AMBER* force field (McDonald and Still, 1992), the GB/SA model for salvation (Still et al., 1990). Cutoff distances for nonbonded interactions were set to 25 Å which resulted in all non-bonded interactions being included. To prevent the peptide-binding host (1b) and alanine guest (2,3 or 4) from drifting apart during the lengthy simulations, flat-bottomed harmonic restraints were applied between the α-carbons of the guest and each of the three α-carbons of the host's amino acid segments. The restraints had force constants of 200 kJ/mol-Å and were centered at 5 Å with a width of ±6 Å. These constraints allowed the α-carbon of the guest to move freely up to ~10 Å from the center of the host before encountering a restoring force from the restraints. Additional flat-bottomed restraints (width=±60°) were used to prevent the host's three C(sp$^2$)S torsions from wandering far from their original (global minimum) torsion angles.

The Monte Carlo/stochastic dynamics (MC/SD) method (Guarnieri et al., 1994) was used to generate the required ensemble averages at 300 K. In this method, random Monte Carlo trial moves (changes in internal coordinates) are made and the resulting structures are accepted or rejected based upon their relative energies using the Metropolis method. Degrees of freedom varied in the Monte Carlo moves of the alanine guest included torsional rotations around its φ and ψ angles and molecular rotations and translations centered on alanine α and carbonyl carbon atoms (made relative to all three Cartesian axes). Guest torsional moves were in the range ±20° to ±180°, and transitions ranged from 0.0 to 1.0 Å. An additional special torsional rotation around the φ angle of the alanine guest was also made which moved only the alanine β-carbon and thus inverted the alanine chirality.

This unusual torsional rotation effected the SME step and transformed the coordinates of a D-alanine into those of L-alanine (or vice versa). Thus, it corresponded to the single-step mutation of one molecule (D-alanine) into another (L-alanine). After the trial moves were made, the Metropolis Monte Carlo procedure was used to accept or reject the new trial structures. Simulations were performed for a total time of 4 ns. The free energy difference of binding of the D- and L-forms of each alanine guest was determined by monitoring an improper torsion ($\zeta$) around the $\alpha$-carbon (N—C—$C_{60}$—$C_\beta$) which has a positive sign for the L-form and a negative sign for the D-form of the peptide. Thus by accumulating the number of times structures had negative and positive $\zeta$ torsion angles during the course of the simulation, the populations (N) of the D- and L-alanine complexes could be determined. The free energy difference of the D- and L-alanine complexes is then obtained from the population using the classical expression:

$$\Delta\Delta G_{(L-D)} = -1.987 * T * \ln(N_{\zeta>0}/N_{\zeta<0})$$

where T is the simulation temperature in degrees Kelvin and $N_{\zeta>0}$ and $N_{\zeta>\zeta}$ are the number of times during the simulation that the angle $\zeta$ has a positive sign (guest alanine is L) and negative sign (guest alanine is D) respectively.

For complexes having differences in the free energy of binding that are large (>>1 kcal/mol), it can be difficult to achieve significant sampling of the higher energy form (here the D-alanine complexes) during a short simulation. To improve the sampling of higher energy structures, a bias energy ($E_{bias}$) was introduced that lowered the energy of the higher energy complex. The bias energy was used only during the Metropolis test in the Monte Carlo part of the MC/SD method and was subtracted from the total energy of any structure where $\zeta$ was negative (hence the higher energy D-alanine complex) in order to improve the sampling of the higher energy forms. The final difference in free energy from these simulations thus becomes:

$$\Delta\Delta G_{(L-D)} = \Delta\Delta G_{(simulation)} + E_{bias}$$

Results

Figure 1:
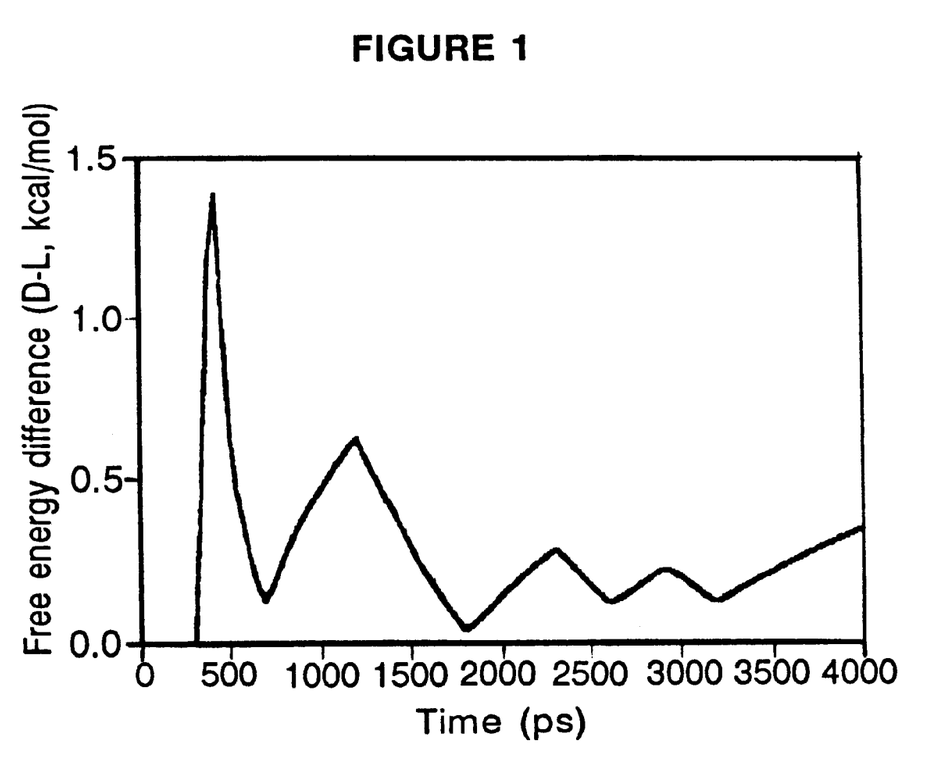
FIG. 1. Calculated free energy difference between binding of D- and L-forms of 2 in complex with 1 over the course of a 4 ns SME simulation (Note—this calculation used $E_{bias}$=2.2 kcal/mol).

Simulations were performed for the complexes of 1b and peptides 2–4. An additional simulation was performed for a conformational isomer of 1 (inv-1) and peptide 2. The results are summarized in Table 1 and FIG. 1 shows the typical development of $\Delta\Delta G_{(L-D)}$ over the course of the simulation. Table 1 also includes the free energy differences as measured by experiment and calculated by the traditional but more time-consuming FEP method.

TABLE 1

Free energy differences (kcal/mol) between the L- and D-forms of alanine peptides 2–5 complexed with host 1 and its inverted form inv-1 as calculated by SME simulations, FEP simulations and from experiment.

| Host | Guest | Ratio D/L | $E_{bias}$ | $\Delta\Delta G_{SME}$ | $\Delta\Delta G_{FEP}$ | $\Delta\Delta G_{expt}$[b] |
|------|-------|-----------|------------|------------------------|------------------------|-----------------------------|
| 1    | 2     | 0.56      | 2.2        | 2.55                   | 2.36 ± 0.4             | 2.2 ± 0.1                   |
| 1    | 3     | 1.49      | 2.5        | 2.36[a]                | 2.56 ± 0.3             | 2.5 ± 0.1                   |
| 1    | 4     | 1.01      | 1.0        | 1.00[a]                | 1.09 ± 0.3             | 0.3 ± 0.2                   |
| inv-1| 2     | 0.46      | 0.0        | 0.46                   | 0.43 ± 0.3             | 0.0 ± 0.2                   |

[a]Average from two 4 ns simulations.
[b]Experiments were performed on 1a.

Conclusions

Figure 2:
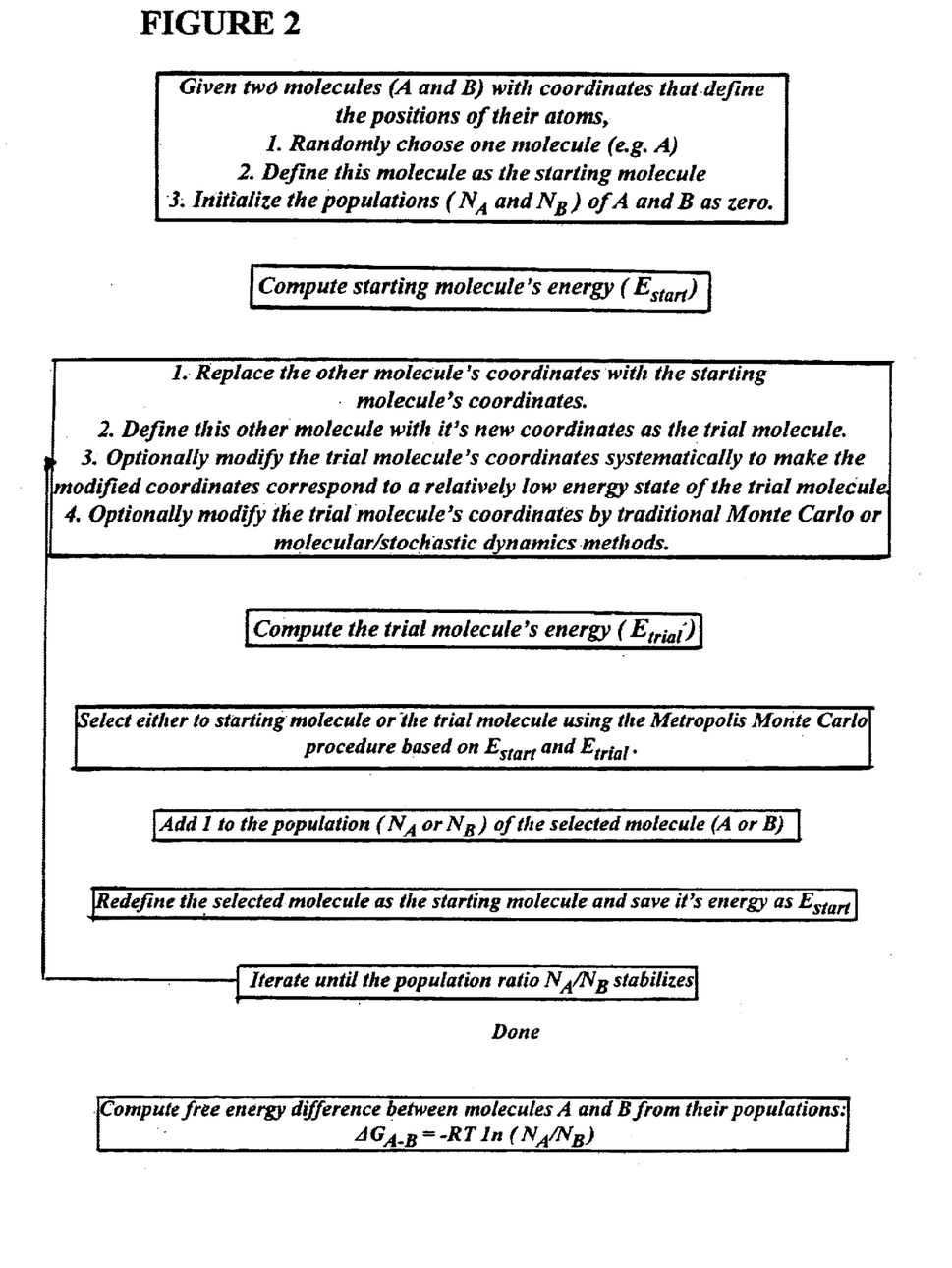
FIG. 2. Flow diagram of one embodiment of the SME simulation.

The results in Table 1 show that the SME method is able to reproduce the experimentally observed enantioselection with an accuracy comparable to the FEP method. While the FEP calculations required 10.5–21 ns of simulation each the SME simulations reached a comparable degree of convergence in only 2–4 ns. Thus SME calculations of free energy differences can be at least 2–10-fold more efficient than the corresponding FEP calculations. See FIG. 2 for a flow diagrammatic representation of one embodiment of the present invention.

REFERENCES

Allen, M. P. and Tildesley, D. J. "Computer Simulation of Liquids," Clarendon Press, Oxford, 1987, pp 110–139.

Chandler, D., "Introduction to Modern Statistical Mechanics," Oxford University Press, New York, 1987, pp 159–183.

Guarnieri, F. and Still, W. C. *J. Comput. Chem.* 1994, 15, 1302.

Kollman, P., *Chem. Rev.* 1993, 93, 2395–2417.

Liu, R. and Still, W. C. *Tetrahedron Lett.* 1993, 34, 2573.

Liu, R. *Philosophical Transactions of the Royal Society Series A,* 1993, 245, 97.

McDonald, D. Q. and Still, W. C., *Tetrahedron Lett.* 1992, 33, 7743.

Senderowitz, H., Guarnieri, F. and Still, W. C., *J. Amer. Chem. Soc.,* 1995, 117, 8211–8219.

Schneider, I., *Genetic and Engineering News,* Oct. 1, 1995,8.

Still, W. C., Tempczyk, A., Hawley, R. C. and Hendrickson, T. *J. Am. Chem. Soc.* 1990, 112, 6127.

van Gunsteren, W. F. and Mark, J. *Eur. J. Biochem.,* 1992, 204, 947–961.

van Gunsteren, W. F. and Weiner, P. K., eds. "Computer Simulation of Biomolecular Systems", ESCOM, 1989, pp 27–59.

Wimmer, E., *Science,* 1995, 269, 1397–1398.

What is claimed is:

1. A method for using a computer which processes data representing physical or energetic characteristics of a first molecule having a first chemical structure and a second molecule having a second chemical structure which is different from the first chemical structure, to determine a free energy difference between the first molecule and the second molecule, the method comprising:

a) selecting a representation of the first molecule with a conformation characterized by a particular set of coordinates that define the position of each atom in the first molecule;

b) determining the energy of the representation of the first molecule;

c) assigning as starting coordinates the coordinates of the representation of the first molecule, transforming randomly the starting coordinates to a set of transformed coordinates, and assigning the transformed coordinates to be the coordinates of a representation of the second molecule to produce a particular conformation of the second molecule characterized by a particular set of coordinates that define the position of each atom in the second molecule;

d) determining the energy of the representation of the second molecule;

e) selecting either the representation of the first molecule or the representation of the second molecule to be added to an ensemble based on the relative energies of the representations of the first molecule and the second molecule, respectively;

f) repeating a) through e) iteratively until a first molecule population in the ensemble and a second molecule population in the ensemble are stabilized; and g) determining the free energy difference between the first molecule and the second molecule by using the stable first molecule and second molecule populations in the ensemble.

2. The method of claim 1, wherein either the first molecule or the second molecule is chosen based on the free energy difference between the first molecule and the second molecule.

3. The method of claim 1, wherein determining the energy of the first molecule or the second molecule is via molecular mechanics, semi-empirical methods or quantum mechanics.

4. The method of claim 1, wherein selecting either the first molecule or the second molecule based on their relative energies comprises a Boltzmann calculation, a probability calculation, a Metropolis transition probability calculation or a Monte Carlo calculation.

5. The method of claim 1, wherein either the first molecule or the second molecule or both molecules are subjected to extrinsic forces from an environment which is either a solvent or a vacuum.

6. The method of claim 1, wherein either the first molecule or the second molecule or both molecules are subjected to extrinsic forces from an environment which is defined by a continuum model for solvation.

7. The method of claim 1, wherein either the first molecule or the second molecule or both molecules are subjected to extrinsic forces from an environment containing a third molecule or molecules.

8. The method of claim 7, wherein the third molecule or molecules is water, an organic solvent, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

9. The method of claim 1, wherein the coordinates are external or internal coordinates.

10. The method of claim 6, wherein the external coordinates are Cartesian coordinates.

11. The method of claim 6, wherein the internal coordinates include bond lengths, bond angles or torsion angles.

12. The method of claim 1, wherein the coordinates of the first molecule are transformed to produce the coordinates of the second molecule with randomization of one or more of the coordinates of the first molecule.

13. The method of claim 1, wherein the coordinates of the first molecule or the coordinates of the second molecule are modified randomly or systematically.

14. The method of claim 1, wherein the coordinates of the first molecule or the coordinates of the second molecule are modified by molecular, stochastic, Langevin or Brownian dynamics.

15. The method of claim 1, wherein dummy atoms are used to represent atoms that are absent in the first molecule but present in the second molecule, or present in the first molecule but absent in the second molecule.

16. The method of claim 1, wherein the first molecule or the second molecule is a biopolymer, a bio-oligomer, a protein, an enzyme, a peptide, a nucleic acid, a carbohydrate, a glycoprotein, a receptor, an organic compound, an inorganic compound, a natural product, a pharmaceutical compound, a drug or a drug candidate, an agrochemical, a herbicide, an insecticide or a component of a chromatography medium.

17. The method of claim 1, wherein the free energy difference is calculated by a computer which processes data representing the physical or energetic characteristics of first molecule and the second molecule and conformations thereof.

18. The method of claim 1, wherein the method is used to select a candidate for a drug, an agrochemical, a synthetic receptor or a catalyst.

19. A method for predicting a relative binding free energy between a first molecule and a second molecule each for a third molecule which comprises using the method of claim 1 with the first molecule free and the second molecule free and with the first molecule and the second molecule interacting with the third molecule or environment.

20. The method of claim 19, wherein the method is performed by a computer which computer processes data which represents the physical or energetic characteristics of the first molecule free and the first molecule interacting with the third molecule and of the second molecule free and the second molecule interacting with the third molecule.

21. An apparatus for determining a free energy difference between a first molecule and a second molecule, the first molecule having a first chemical structure and the second molecule having a second chemical structure which is different from the first chemical structure, the apparatus comprising:

a) a means of selecting a representation of the first molecule with a conformation characterized by a particular set of coordinates that define the position of each atom in the first molecule;

b) a means of determining the energy of the representation of the first molecule;

c) a means of assigning as starting coordinates the coordinates of the representation of the first molecule, transforming randomly the starting coordinates to a set of transformed coordinates, and assigning the transformed coordinates to be the coordinates of a representation of the second molecule to produce a particular conformation of the second molecule characterized by a particular set of coordinates that define the position of each atom in the second molecule;

d) a means of determining the energy of the representation of the second molecule, and selecting either the representation of the first molecule or the representation of the second molecule to be added to an ensemble based on the relative energies of the representations of the first molecule and the second molecule, respectively, wherein (i) selections of the representations of the first and second molecules, respectively, (ii) determinations of the respective energies and (iii) selection of either the representation of the first molecule or the representation of the second molecule to be added to the ensemble based on the relative energies of the representations are repeated iteratively until a first molecule population in the ensemble and a second molecule population in the ensemble are stabilized, and the free energy difference between the first molecule and the second molecule is determined by using the stable first molecule and second molecule populations in the ensemble.

22. The apparatus of claim 21, wherein either the first molecule or the second molecule is chosen based on the free energy difference between the first molecule and the second molecule.

* * * * *